United States Patent [19]

Voorhees et al.

[11] 4,201,788

[45] May 6, 1980

[54] PROCESS FOR ALLEVIATING PROLIFERATIVE SKIN DISEASES

[75] Inventors: John J. Voorhees, Ann Arbor, Mich.; Diane H. Russell, Tucson, Ariz.

[73] Assignees: University Patents, Inc., Stamford, Conn.; The Regents of the University of Michigan, Ann Arbor, Mich.

[21] Appl. No.: 932,878

[22] Filed: Aug. 11, 1978

Related U.S. Application Data

[63] Continuation-in-part of Ser. No. 734,152, Oct. 20, 1976, abandoned.

[51] Int. Cl.² .................... A61K 31/275; A61K 31/15
[52] U.S. Cl. .................... 424/304; 424/203; 424/240; 424/273 R; 424/319; 424/326; 424/327
[58] Field of Search ................ 424/319, 326, 327, 304

[56] References Cited

U.S. PATENT DOCUMENTS

| | | | |
|---|---|---|---|
| 4,007,268 | 2/1977 | Voorhees | 424/200 |
| 4,009,282 | 2/1977 | Voorhees | 424/317 |
| 4,034,087 | 7/1977 | Voorhees | 424/240 |

OTHER PUBLICATIONS

Cancer Research, 34, 886–892, (1974).
Biochimica et Biophysica Acta, 473, (1978), 241–293.
Handbook of Non-Prescription Drugs, 5th ed., 332, (1977).
Physicians Desk Reference, 26th ed., pp. 809–811, (1972).

*Primary Examiner*—Leonard Schenkman
*Attorney, Agent, or Firm*—Neal A. Waldrop

[57] ABSTRACT

A process and pharmaceutical compositions for alleviating proliferative skin diseases such as psoriasis, atopic dermatitis, etc., comprising administering to humans or domesticated animals, topically and/or parenterally, and/or systemically a composition comprising a pharmaceutical carrier and at least one diamino compound selected from the diamines of saturated and unsaturated aliphatic hydrocarbons having 3 to 6 carbon atoms and the diamines of saturated monocarboxylic acids having 4 to 6 carbon atoms and the alkyl esters thereof containing from 1 to 4 carbon atoms. These diamino compounds are usable alone or in combination with certain prostaglandin compounds, certain phosphodiesterase inhibitor compounds and certain cyclic adenosine monophosphate compounds.

7 Claims, No Drawings

PROCESS FOR ALLEVIATING PROLIFERATIVE SKIN DISEASES

CROSS REFERENCE TO RELATED APPLICATION

This application is a continuation-in-part of United States Ser. No. 734,152, filed Oct. 20, 1976, now abandoned.

BRIEF DESCRIPTION OF THE INVENTION

This invention relates to pharmaceutical compositions for application to the skin and to a method for the treatment of proliferating skin diseases. The compositions may be applied topically, or by injection such that the composition enters the blood stream or intralesionally, intradermally, or sub-cutaneously or orally. The treatment can be either therapeutic or prophylactic.

DETAILED DESCRIPTION OF THE INVENTION

Proliferative skin diseases are widespread throughout the world and afflict millions of humans and their domesticated animals. This invention provides a method for treatment of such diseases and pharmaceutical compositions which are useful in alleviating them. As used hereinafter in this specification and in the claims, the expression "proliferative skin diseases" means benign and proliferative skin diseases which are characterized by epidermal cell proliferation, or division, and may also be associated with incomplete tissue differentiation. Psoriasis is the most serious of the skin diseases with which this invention is concerned. Such diseases include: psoriasis, atopic dermatitis, non-specific dermatitis, primary irritant contact dermatitis, allergic contact dermatitis, lamellar ichthyosis, epidermolytic hyperkeratosis, premalignant sun induced keratosis, non-malignant keratosis, and seborrheic dermatitis in humans and atopic dermatitis and mange in domesticated animals.

Heretofore, proliferative skin diseases have been generally accepted by mankind as an ongoing evil having degrees of severity variable with time, with inherited skin traits and external factors but always have been recognized as unsightly, painful, morbid diseases. Over the history of mankind innumerable medicines and treatments have been proposed, tried and used with varying degrees of success. However, no treatment heretofore devised or pharmaceutical composition used has been entirely successful in the wide spectrum of specific diseases encompassed by the expression proliferative skin diseases.

The present day treatments of a commercial nature which are prescribed and used for the treatment of proliferative skin diseases include three approaches: (1) topical applications: coal tar derivatives, 5 fluorouracil, vitamin A acid, glucocorticoids in high dosage (constituting a nonpermissive concentration), bath oils and non-specific emollient creams and ointments; (2) the systemic administration: glucocorticoids and classic anti-cancer agents, for example, methothrexate, hydroxyurea, azaribine, cyclophosphamide; (3) physical modalities: ultra violet light, x-irradiation, and in severe cases, surgery.

While these treatments provide, in certain cases, some remission of the original symptoms, each treatment suffers some defect, for example, temporary and incomplete mititgation of symptoms, rapid re-occurrence of the disease when mitigation is terminated, serious and sometimes irreversible damage (atrophy) resulting from the topical application for extended times of glucocorticoids, acute bone marrow supression and cirrhosis of the liver resulting from the protracted use of methothrexate which may lead to death of the patient, and the causation of cancer by the application of anti-cancer drugs, x-irradiation, or ultra violet rays.

In accordance with this invention it has been found the proliferative skin diseases are alleviated, that is, the symptoms of the disease are noticeably improved or become undetectable by the treatment of the afflicted patient, or animal, with one or more of the pharmaceutical compositions described in detail hereinbelow.

For the purposes of this specification and the claims, a proliferative skin disease is alleviated when there is a noticeable decrease in the thickness of a lesion to palpation, with or without residual redness, or residual slightly dilated blood vessels or residual hyper- or hypo-pigmentation. For purposes of this invention and the claims hereof, psoriasis is alleviated when a scale-free psoriasis lesion is noticeably decreased in thickness, or noticeably but incompletely cleared or completely cleared.

The compositions may be applied topically or by injection such that the composition enters the blood stream, or intradermally, intra- or peri-lesionally, or sub-cutaneously. The preferred method of application is topically.

The term "topical" as employed herein relates to the use of the active ingredient incorporated in a suitable pharmaceutical carrier, and applied at the site of the disease for exertion of local action. Accordingly, such topical compositions include those pharmaceutical forms in which the compound is applied externally by direct contact with the skin surface to be treated. Conventional pharmaceutical forms for this purpose include ointments, lotions, pastes, jellies, sprays, aerosols, bath oils and the like. The term "ointment" embraces formulations (including creams) having oleaginous, absorption, water-soluble and emulsion-type bases, e.g., petrolatum, lanolin, polyethylene glycols, as well as mixtures thereof. It has been found that topical application with occlusion of an area larger than the medicated area produces improved results relative to nonoccluded topical application and is, therefore, the preferred method of topical treatment with the compositions of this invention.

Certain of the compositions of this invention advantageously include skin penetrating adjuvants such as, for example, dimethyl sulfoxide, dimethyl acetamide, etc.

Injection "intradermally" refers to positioning the composition in the high dermis by needle injection, or by high pressure air injection.

Injection "intra- or peri-lesionally" refers to positioning the composition into the lesion or into the tissue adjacent to the lesion.

The compositions may be injected so as to reach the blood stream intramuscularly, sub-cutaneously, rectally by suppositories, sublingually, intravenously, orally, by inhalation, or by application to non-diseased skin.

The best mode of practicing the process of this invention is to treat the afflicted animal, or human, so as to cause a continuing release of the active compound at the afflicted site or sites, at a selected, controlled rate which is sustained for an extended time period. Sustained release of the alleviating composition of this invention when topically applied may be accomplished by appropriate selection of a mixture of absorption adjuvants and non-adsorption adjuvants to insure availability of a small proportion of the total composition applied at any instant after application and continuously until the total active compounds therein have penetrated the skin.

The compositions of this invention comprise a pharmaceutical carrier and about 0.1% to about 15%, weight/volume, of at least one diamino compound selected from the diamines of saturated and unsaturated aliphatic hydrocarbons having 3 to 6 carbon atoms and the diamines of saturated monocarboxylic acids having 4 to 6 carbon atoms and the alkyl esters thereof containing from 1 to 4 carbon atoms. A preferred sub-group comprises ornithine and the analogs of ornithine, including α-methyl ornithine, α-hydrazino ornithine, αhydrazino- α-methyl ornithine, trans-3-dehydro-D,L-ornithine, DL-α-difluoromethyl ornithine and N-(5'-phosphophyridoxyl)- ornithine.

The compositions of this invention also comprise a pharmaceutircal carrier and about 0.1 to about 15% w/v of methyl glyoxal bis-(guanyl hydrazone) or 1,1'-(methylethanediylidinedinitrilo)-bis-(3-aminoguanidine) as the sole active compound or a mixture of one or more thereof.

Satisfactory diamino aliphatic hydrocarbons include 1,3 diaminopropane, 1,4 diaminobutane, 1,5 diaminopentane and 1,6 diaminohexane and the corresponding unsaturated compounds. They may be applied separately or in admixture and preferably are applied topically. In treating psoriasis, better alleviation is obtained from topical application, preferably with occlusive bandage, of admixtures of a diamino aliphatic hydrocarbon with one or more of the analogs of ornithine, preferably α-methyl ornithine, or DL-α-difluoromethyl ornithine, or both. Excellent alleviation of psoriasis is obtained from compositions comprising a mixture of α-methyl ornithine and methylglyoxal bis-(guanyl hydrazone) or a mixture of DL-α-difluoromethyl ornithine and 1,1'-(methylethanediylidinedinitrilo)-bis-(3-aminoguanidine).

These diamines alleviate proliferative skin diseases primarily through reduction of cell proliferation or division and have variable degrees of effectiveness dependent upon the particular active compound or mixture of compounds which is selected, the concentration thereof in the administered composition and the seriousness of the proliferative skin disease being treated, psoriasis being the most serious. They fall into the functional category of ornithine decarboxylase anti-enzymes in the skin and appear to function similarly when administered to a human or animal afflicted with a proliferative skin disease. Similar beneficial alleviation of psoriasis is obtained by diamine-ketones having 3–6 carbon atoms, and 1,4 diaminobutanone is preferred.

The compositions of this invention also comprise a pharmaceutircal carrier and about 0.1% to about 15% w/v of at least one of the diamino compounds above identified in admixture with at least one of the compounds selected from the groups:

I A Compound of the formula

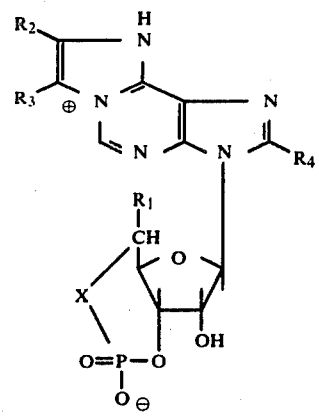

wherein $R_1$ is H or methyl; $R_2$ is H or phenyl; $R_3$ is propyl, isopropyl or phenyl; $R_4$ is H, bromine, methylthio, or benzylthio, X is oxygen or methylene;

II A compound of the formula

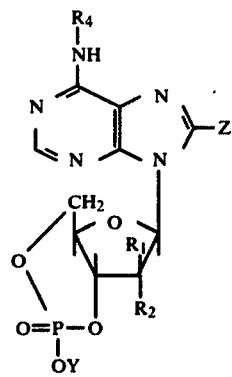

wherein $R_1$ and $R_2$ are hydrogen or hydroxyl; Y is hydrogen or alkali metal; Z is hydrogen, benzylthio, thiol, halogen, alkylthio wherein alkyl is from 1 to 8 carbon atoms, inclusive, and hydroxy; $R_4$ is hydrogen,

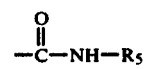

wherein $R_5$ is phenyl, benzyl, or alkyl of 1 to 8 carbon atoms;

III A compound of the formula

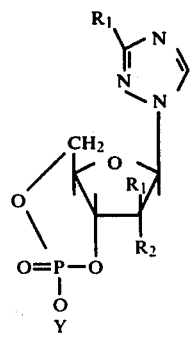

wherein $R_1$ is $-CONH_2$, $-CSNH_2$, $-C(NH)NH_2$, $-C(NH)NHOH$, $-CN$, or $-COOCH_3$; $R_1$ and $R_2$ are hydrogen or hydroxy; Y is hydrogen or alkali metal.

IV A compound selected from the group consisting of compounds characterized by the formula

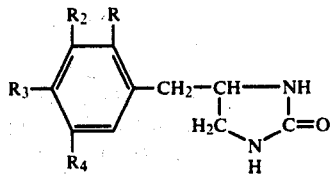

wherein R is halogen, hydrogen, lower alkyl and lower alkoxy; $R_2$, $R_3$ and $R_4$ taken independently of each other are hydrogen, lower alkoxy or hydroxy-lower alkoxy and provided that $R_2$, $R_3$ and $R_4$ taken independently of each other represent at least one oxygenated substituent; or R, $R_2$, $R_3$ and $R_4$ taken as an adjacent pair is methylenedioxy and the optical antipodes thereof. A preferred compound from this group is DL-4(3-butoxy-4-methoxybenzyl)-2-imidazolidinone.

V. Prostaglandin compounds of the D-type (PGD) and E-type (PGE) selected from the group consisting of $PGE_1$, $PGE_2$, $PGE_3$ or the alkyl ester thereof containing from 1 to 8 carbon atoms inclusive, or 13, 14-dihydro $PGE_1$ or the alkyl esters thereof containing from 1 to 8 carbon atoms inclusive, and $PGD_2$ and the alkyl esters thereof containing from 1 to 8 carbon atoms inclusive.

The method of this invention may be carried out satisfactorily by administering to a patient afflicted with a proliferative skin disease, on a concurrent basis, at least one of the analogs of ornithine, or methylglyoxal bis-(guanylhydrazone), or a mixture thereof, and one or more of the compounds represented by the above Groups I-V inclusive. In certain cases, the method of the invention may involve the administration of compositions containing a single active compound or a mixture of active compounds by a plurality of the forms of the administration, for example, by a combination of topical and/or oral and/or injection.

The compositions of this invention may also be employed in conjunction with glucocorticoids. The expression "glucocorticoids" refers to a naturally occurring product of the adrenal cortex, or a synthetic analog thereof possessing anti-inflammatory activity and minimal or no mineralocorticoid activity or sex steroid activity. Of the natural glucocorticoids, one may use for example, hydrocortisone or the synthetic glucocorticoids such as methyl prednisolone acetate "Medrol" for oral application or triamcinolone for topigal therapy. The glucocorticoids should be employed in minor amounts or "permissive dosage". The expression "permissive dosage" for glucocorticoids refers to a quantity which minimally supplements the natural output of adrenal cortical glucocorticoids in a normal person and which dosage administered alone, has no perceptible effect on proliferative skin diseases.

The quantity of the active compound to be used in the compositions of this invention for administration topically, parenterally or systemically ranges from about 0.1% to about 15% weight/volume topically; from about 0.1% to about 10% w/v parenterally; and for oral dosage forms the % amount of active ingredient is determined by the physical characteristics of the carrier with due regard to manufacturing requirements and elegance.

The compositions of the present invention are presented for systemic administration to humans and animals in unit dosage forms, such as tablets, capsules, pills, powders, granules, sterile parenteral solutions or suspensions, and oral solutions or suspensions, and oil-water emulsions containing suitable quantities of one or more of the active compounds above described.

For oral administration either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. The tablets can be laminated or otherwise compounded to provide a dosage form affording the advantage of prolonged or delayed action or predetermined successive action of the enclosed medication. For example, the tablet can comprise an inner dosage and an outer dosage component, the latter being in the form of an envelope over the former.

Alternatively, the two component system can be utilized for preparing tablets containing two or more compatible active ingredients. Wafers are prepared in the same manner as tablets, differing only in shape and the inclusion of sucrose or other sweetener and flavor. In their simplest embodiment, capsules, like tablets, are prepared by mixing the active compound or compounds with an inert pharmaceutical diluent and filling the mixture into a hard gelatin capsule or appropriate size. In another embodiment, capsules are prepared by filling hard gelatin capsules with polymeric acid coated beads containing the active compound or compounds. Soft gelatin capsules are prepared by machine encapsulation of a slurry of the active compound or compounds with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared of the insoluble forms with a syrup vehicle with the aid of a suspending agent such as acacia, tragacanth, methylcellulose and the like.

Topical ointments can be prepared by dispersing the active compound or compounds in a suitable ointment base such as petrolatum, lanolin, polyethylene glycol, mixtures thereof, and the like. Advantageously, the active compound or compounds is finely divided by means of a colloid mill utilizing light liquid petrolatum as a levigating agent prior to dispersing in the ointment base. Topical creams and lotions are prepared by dispersing the active compound or compounds in the oil phase prior to the emulsification of the oil phase in water.

For parenteral administration the dosage forms are prepared utilizing the active compound or compounds and a sterile vehicle, water being preferred. The compound depending on the form and concentration used, can be either suspended or dissolved in the vehicle. In preparing solutions, a water-soluble form of the compound can be dissolved in water for injection and filter sterilized before filling into a suitable vial or ampule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution.

For parenteral or systemic administration of the compositions of this invention, the usual dosage of the selected active compound, or compounds, should be employed.

In some cases the method of this invention is advantageously practiced by combining the administration forms in a time spaced sequence, for example, by using systemic application of one or more of the compositions for a time period and then applying one or more compositions topically, or by injection while continuing the systemic application, etc.

The following examples identify certain compositions which typify the manner of combining selected active compounds with a pharmaceutical carrier for use in the process of treatment of proliferative skin diseases as above generally described, but they are not intended to represent the limits of either the compositions of or the process of this invention which is defined in the claims.

EXAMPLE 1

Topical Ointment

α-methyl ornithine: 50 gm.
Liquid petrolatum (heavy): 250 gm.
Wool fat: 200 gm.
White petrolatum q.s.: 1000 gm.

The white petrolatum and wool fat are melted and 100 gm. of liquid petrolatum added thereto. The α-methyl ornithine is added to the remaining liquid petrolatum and the mixture milled until the powder is finely divided and uniformly dispersed. The powder mixture is stirred into the white petrolatum mixture and stirring continued until the ointment congeals.

The foregoing ointment is usefully applied topically to psoriatic lesions on the skin of humans, preferably two to four times daily with occlusive bandage.

EXAMPLE 2

Cream

One thousand grams of a topical cream is usefully prepared from the following types and amounts of ingredients:
α-methyl ornithine: 100 gm.
Tegacid Regular*: 150 gm.
Spermaceti: 100 gm.
Propylene glycol: 50 gm.
Polysorbate 80: =gm.
Methylparaben: 1 gm.
Deionized water q.s.: 1000 gm.

*Self-emulsifying glyceryl monostearate from Goldschmidt Chemical Corporation, New York, N.Y.

The Tegacid and spermaceti are melted together at a temperature of 70–80 degrees C. The methylparaben is dissolved in about 500 gm. of water and the propylene glycol, polysorbate 80, and α-methyl ornithine are added in turn, maintaining a temperature of 75–80 degrees C. The methylparaben mixture is added slowly to the Tegacid and spermaceti melt, with constant stirring. The addition is continued for at least 30 minutes with continued stirring until the temperature has dropped to 40–45 degrees C. The pH of the final cream is adjusted to 3.5 by adding 2.5 gm. of citric acid and 0.2 gm. of dibasic sodium phosphate dissolved in about 50 gm. of water. Finally, sufficient water is added to bring the final weight to 1000 gm. and the preparation stirred to maintain homogeneity until cooled and congealed.

α-methyl ornithine is satisfactorily replaced in the above composition by an equal amount of 1,3 diaminopropane, or 1,4 diaminobutane, or 1,5 diaminopentane, or 1,6 diaminohexane, or admixtures thereof to a total of up to 200 grams.

The foregoing compositions are useful for the treatment of psoriasis by applying to the lesions with occlusive bandage.

EXAMPLE 3

Topical Ointment

Methyl glyoxal bis-(guanyl hydrazone): 50 gm.
Liquid petrolatum (heavy): 250 gm. 'Wool fat: 200 gm.
White petrolatum q.s.: 1000 gm.

The white petrolatum and wool fat are melted and 100 gm. of liquid petrolatum added thereto. The methyl glyoxal bis-(guanyl hydrazone) is added to the remaining liquid petrolatum and the mixture milled until the powder is finely divided and uniformly dispersed. The powder mixture is stirred into the white petrolatum mixture and stirring continued until the ointment congeals.

The foregoing ointment is usefully applied topically to psoriatic lesions on the skin of humans, preferably two to four times daily with occlusive bandage.

EXAMPLE 4

Topical Ointment 1,1'-(methylethanediylidinedinitrilo)-bis-(3-aminoguanidine): 50 gm.
Liquid petrolatum (heavy): 250 gm.
Wool fat: 200 gm.
White petrolatum q.s.: 1000 gm.

The white petrolatum and wool fat are melted and 100 gm. of liquid petrolatum added thereto. The 1,1'-methylethanediylidinedinitrilo)-bis-(3-aminoguanidine) is added to the remaining liquid petrolatum and the mixture milled until the powder is finely divided and uniformly dispersed. The powder mixture is stirred into the white petrolatum mixture and stirring continued until the ointment congeals.

The above composition may be modified to contain about 5 to 50 grams methyl glyoxal bis-(guanyl hydrazone).

The foregoing ointment is usefully applied topically to psoriatic lesions on the skin of humans, preferably two to four times daily with occlusive bandage.

EXAMPLE 5

Capsules

One thousand two-piece hard gelatin capsules for oral use, each containing 200 mg. of α-methyl ornithine are prepared from the following types and amounts of materials:

α-methyl ornithine: 200 gm.
Corn starch: 150 gm.
Talc: 75 gm.
Magnesium stearate: 2.5 gm.

The materials are thoroughly mixed and then encapsulated in the usual manner.

The foregoing capsules are useful for the systemic treatment of psoriasis in adult humans by the oral administration of 1 capsule every 4 hours.

Using the procedure above, capsules are similarly prepared containing in 5, 100, and 500 mg. amounts by substituting 5, 100, and 500 gm. of α-methyl ornithine for the 200 gm. used above.

EXAMPLE 6

Capsules

One thousand two-piece hard gelatin capsules for oral use, each containing 200 mg. of α-methyl ornithine and 200 mg. of DL-α-difluoromethyl ornithine are prepared from the following types and amounts of ingredients:

α-methyl ornithine: 200 gm.
DL-α-difluoromethyl ornithine: 200 gm.
Corn starch: 250 gm.
Talc: 75 gm.
Magnesium stearate: 2.5 gm.

The ingredients are thoroughly mixed and then encapsulated in the usual manner.

The foregoing capsules are useful for the systemic treatment of psoriasis in adult humans by the oral administration of 1 capsule twice a day.

EXAMPLE 7

Tablets

α-methyl ornithine: 500 gm.
trans-3-dehydro-DL-ornithine: 100 gm.
Lactose: 125 gm.
Corn starch: 65 gm.
Magnesium stearate: 7.5 gm.
Light Liquid petrolatum: 3 gm.

The ingredients are thoroughly mixed and slugged. The slugs are broken down by forcing through a number sixteen screen. The resulting granules are then compressed into tablets, each tablet containing 200 mg. of α-methyl ornithine and 100 mg. of trans-3-dehydro-DL-ornithine.

The foregoing tablets are useful or systemic treatment of psoriasis in adult humans by oral administration of 1 tablet every 4 hours.

EXAMPLE 8

Oral Syrup

One thousand cc. of an aqueous suspension for oral use, containing in each 5 cc. dose 200 mg. of α-methyl ornithine is prepared from the following types and amounts of ingredients:

α-methyl ornithine: 40 gm.
Citric acid: 2 gm.
Benzoic acid: 1 gm.
Sucrose: 700 gm.
Tragacanth: 5 gm.
Lemon oil: 2 cc.
Deionized water q.s.:

The citric acid, benzoic acid, sucrose, tragacanth, and lemon oil are dispersed in sufficient water to make 850 cc. of solution. The α-methyl ornithine is stirred into the syrup until uniformly distributed. Sufficient water is added to make 1000 cc.

The composition so prepared is useful in the systemic treatment of psoriasis in adult humans at a dose of 1 teaspoonful 4 times a day.

EXAMPLE 9

Parenteral solution

A sterile aqueous solution for intramuscular use, containing in 1 cc. 75 mg. of α-methyl ornithine is prepared from the following types and amounts of materials:

α-methyl ornithine: 75 gm.
Lidocaine hydrochloride: 4 gm.
Methylparaben: 2.5 gm.
Propylparaben: 0.17 gm.
Water for injection q.s.: 1000 cc.

The ingredients are dissolved in the water and the solution sterilized by filtration. The sterile solution is filled into vials and the vials sealed.

The composition is useful in the systemic treatment of psoriasis at a dose of 1 cc. I.M. 4 times a day.

EXAMPLE 10

Parenteral solution

A sterile aqueous solution for intradermal use, containing in 1 cc 5 mg. of α-methyl ornithine is prepared from the following types and amounts of ingredients:

α-methyl ornithine: 5 gm.
Sodium chloride 10% solution q.s.:
Water for injection q.s.: 1000 cc.

The α-methyl ornithine is added to the water and sufficient sodium chloride added to form an isotonic solution and the solution sterilized by filtration.

The sterile solution is administered intradermally by by pressure injection for treatment of psoriasis.

EXAMPLE 11

Cream

α-methyl ornithine: 1000 gm.
trans-1,4 diamino-2-butene: 500 gm.
Cetyl alcohol: 600 gm.
Stearyl alcohol: 600 gm.
Aerosol OT: 150 gm.
White petrolatum: 3000 gm.
Propylene Glycol: 1000 ml.
Distilled Water q.sl.: 10000 gm.

The α-methyl ornithine and trans-1,4 diamino-2-butene are mixed with the white petrolatum and stirred into a melt of the alcohols and propylene glycol. The aerosol OT is dissolved in 5000 cc. of water and an emulsion formed with the petrolatum mix, sufficient water being added to make 10,000 gm.

The cream is applied to psoriatic lesions twice daily with occlusive bandage.

Optionally following the procedure of the preceding example substituting 2,000 grams of dimethylacetamide for 2000 grams of water, or 200–500 grams of dimethylsulfoxide for 200–500 grams of water, a composition is obtained providing better penetration of the active ingredients into the skin.

EXAMPLE 12

One thousand two-piece hard gelatin capsules for oral use, each containing 200 mg. of methyl glyoxal bis-(guanyl hydrazone) are prepared from the following types and amounts of materials:

Methyl glyoxal bis-(guanyl hydrazone): 200 gm.
Corn starch: 150 gm.
Talc: 75 gm.
Magnesium stearate: 2.5 gm.

The α-methyl ornithine capsules prepared to the formulation of Example 5 and the capsules prepared in accordance with this example are useful for the systemic treatment of psoriasis in adult humans by the oral administration of one of each capsule twice a day.

EXAMPLE 13

One thousand two-piece hard gelatin capsules for oral use each containing 200 mg. of 8-methylthio cAMP are pkking types and amounts of ingredients:

8-methylthio cAMP: 200 gm.
Corn starch: 250 gm.
Talc: 75 gm.
Magnesium stearate: 2.5 gm.

The ingredients are thoroughly mixed and then encapsulated in the usual manner.

The foregoing capsules are useful for the systemic treatment of psoriasis in adult humans by the oral administration of 1 capsule twice a day.

Psoriasis is alleviated by orally administering concurrently one capsule containing the 8-methylthio cAMP, one capsule formulated to contain α-methyl ornithine, as shown above in Example 5 and one capsule containing methyl glyoxal bis (guanyl hydrazone) prepared to the formulation of Example 12, twice per day.

EXAMPLE 14

Cream 1000 grams of a topical cream is usefully prepared from the following types and amounts of ingredients:

1 α-methyl ornithine: 100 grams
Hydrocortisone: 10 grams
Tegacid Regular: 150 grams
Spermaceti: 100 grams
Propylene glycol: 50 gm.
Polysorbate 80: 5 gm.
Methylparaben: 1 gm.
Deionized water q.s.: 1000 gm.

The 60-methyl ornithine and hydrocortisone are added to the other components in the same manner described above in the preparation of the cream of Example 2. This composition, applied topically to psoriatic lesions on the skin of humans, with occlusive bandage, is particularly effective in alleviating aggrevated cases of psoriasis. Similar results are obtained by substituting for the 10 grams of hydrocortisone with 0.10 grams of triamcinolone.

Good results in alleviating psoriasis are also obtained by topical application of the cream of Example 2, in conjunction with the application of a permissive dose of hydrocortisone, that is, a concentration of hydrocortisone between about one-eighth to one-half the concentration employed in this example.

EXAMPLE 15

α-methyl ornithine: 100 grams
Hydrocortisone: 10 grams
D,L-4(3-butyoxy-4-methoxybenzyl)-2-imidazolidinone: 100 grams
Tegacid Regular: 150 grams
Spermaceti: 100 grams
Propylene8glycol: 51 grams
Polysorbate 80: 5 gm.
Methylparaben: 1 gm.
Deionized water q.s.: 1000 gm.

This composition, applied topically to psoriatic lesions on the skin of humans, with occlusive bandage, is particularly effective in alleviating aggrevated cases of psoriasis.

Good results are obtained on somewhat less aggrevated cases of psoriasis by modifying the above described composition to contain concentrations of D,L-4(3-butyoxy-4-methoxybenzyl)-2-imidazolidinone as low as one-eighth of the concentration above used; in certain cases, it is also desirable to increase the concentration thereof to as high as about 5% of the composition.

For topical application improved alleviation, particularly alleviation of psoriasis, is obtained by incorporating skin penetrants in the composition(of the type above illustrated in Example 9. It has been found that skin penetration is also improved by selecting as the active component a diamino compound in ester form, for example, α-methyl ornithine tert-butyl ester or DL-α-difluoromethyl ornithine tert-butyl ester. Such esters are satisfactorily prepared by the following procedure: a suspension was prepared containing 3.7 grams of $N^2$, $N^5$-bis(benzyloxy carbonyl)-2-5-diamino-2-methyl pentanoic acid in 250 cc. of methylene chloride and 0.5 ml. of sulfuric acid. To this suspension isobutylene gas was added until no further volume change occurred, requiring about 40–50 ml. The reaction mixture was capped and stirred for 72 hours at room temperature. Then ammonia gas was added to bring the pH to 8, and excess isobutylene was removed with a nitrogen stream. The reaction mixture was washed with water, dried over anhydrous calcium sulfate, and evaporated to provide an oil. After prolonged storage at 0° C., the oil crystallized from ethanol-water was analyzed and found to be α-methyl ornithine tert-butyl ester. The starting compound was prepared from α-methyl ornithine hydrochloride by the procedure described on page 1586, Journal of Pharmaceutical Sciences, Vol. 66, No. 11, Nov. 1977.

We claim:

1. A process for treating non-malignant proliferative skin diseases which comprises administering to the afflicted human or animal, a composition containing as an active component at least one compound selected from the group consisting of methyl glyoxal bis-(guanyl hydrazone) and 1,1'-methylethanediylidinedinitrilo)-bis-(3-aminoguanidine), said compound being in association with a pharmaceutical carrier wherein the concentration of said active component is effective to alleviate a proliferative skin disease.

2. A process in accordance with claim 1 wherein said active component is methyl glyoxal bis-(guanyl hydrazone).

3. A process in accordance with claim 1 wherein said active component is 1,1'-methylethanediylidinedinitrilo-bis-(3-aminoguanidine).

4. A process for treating non-malignant proliferative skin diseases which comprises administering to the afflicted human or animal, a composition containing as an active component at least one compound selected from the group consisting of methyl glyoxal bis(guanyl hydrazone) and 1,1'-methylethanediylidinedinitrilo)-bis-(3-aminoguanidine), and a minor amount of a glucocorticoid, said compounds being in association with a pharmaceutical carrier wherein the concentration of said active component is effective to alleviate a proliferative skin disease.

5. A process for treating non-malignant proliferative skin diseases which comprises administering to the afflicted human or animal, a composition containing as an active component at least one of the compounds selected from the groups consisting of;

I A compound of the formula

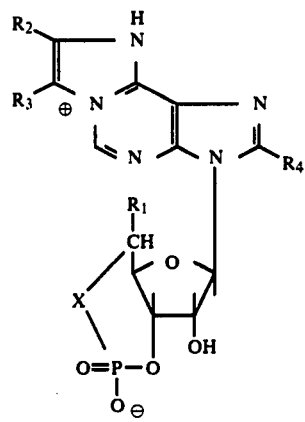

wherein $R_1$ is H or methyl; $R_2$ is H or phenyl; $R_3$ is propyl, isopropyl or phenyl; $R_4$ is H, bromine, methylthio, or benzylthio; X is oxygen or methylene;

II a compound of the formula

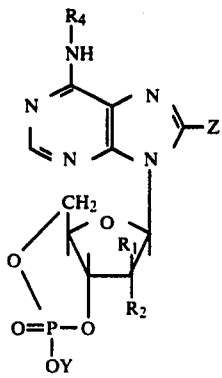

wherein $R_1$ and $R_2$ are hydrogen or hydroxyl; Y is hydrogen, or alkali metal; Z is hydrogen, benzylthio, thiol, halogen, alkylthio wherein alkyl is from 1 to 8 carbon atoms, inclusive, and hydroxy; $R_4$ is hydrogen,

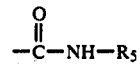

wherein $R_5$ is phenyl, benzyl or alkyl of 1 to 8 carbon atoms;

III A compound of the formula

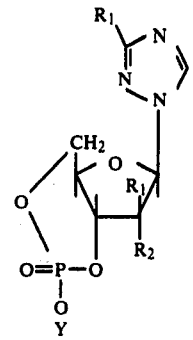

wherein $R_1$ is —CONH$_2$, —C(NH)NH$_2$, —C(NH)NHOH, —CN, or —COOCH$_3$; $R_1$ and $R_2$ are hydrogen or hydroxy; Y is hydrogen or alkali metal;

IV a compound selected from the group consisting of compounds characterized by the formula

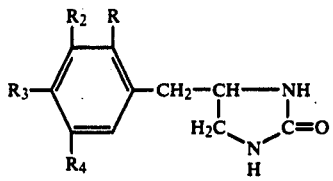

wherein R is halogen, hydrogen, lower alkyl and lower alkoxy; $R_2$, $R_3$ and $R_4$ taken independently of each other are hydrogen, lower alkoxy or hydroxy-lower alkoxy and provided that $R_2$, $R_3$ and $R_4$ taken independently of each other represent at least one oxygenated substitutent; or R, $R_2$, $R_3$ and $R_4$ taken as an adjacent pair is methylenedioxy and the optical antipodes thereof, and V Prostaglandin compounds of the D-type (PGD) selected from the group consisting of PGE$_1$, PGE$_2$, PGE$_3$ or the alkyl ester thereof containing from 1 to 8 carbon atoms inclusive, or 13, 14-dihydro PGE$_1$ or the alkyl esters thereof containing from 1 to 8 carbon atoms inclusive, and PGD$_2$ and the alkyl esters thereof containing from 1 to 8 carbon atoms inclusive, and at least one compound selected from the group consisting of methyl glyoxal bis-(guanyl hydrazone) and 1,1'-methylethanediylidinedinitrilo-bis-(3-aminoguanidine), said compounds being in association with a pharmaceutical carrier wherein the concentration of said active component is effective to alleviate a proliferative skin disease.

6. A process in accordance with claim 5 wherein said compound is methyl glyoxal bis-(guanyl hydrazone).

7. A process in accordance with claim 5 wherein said active component is 1,1'-methylethanediylidinedinitrilo-bis-(3-aminoguanidine).

UNITED STATES PATENT AND TRADEMARK OFFICE
CERTIFICATE OF CORRECTION

PATENT NO. : 4,201,788
DATED : May 6, 1980
INVENTOR(S) : John J. Voorhees et al.

It is certified that error appears in the above—identified patent and that said Letters Patent is hereby corrected as shown below:

Column 1, line 67, "mititgation" should read -- mitigation --

Column 5, line 32, "cqrbon" should read -- carbon --.

Column 5, line 54, "topigal" should read -- topical --.

Column 7, line 66 "=" should read -- 5 --.

Column 8, line 31, "'" should be deleted.

Column 11, line 23, after "are" insert -- prepared from the following --.

Column 11, line 23, delete "pkking".

Column 12, line 9, delete "8".

Column 12, line 9, delete "51 grams" and insert -- 50 grams-

Column 12, line 27, after "composition" delete ")".

Signed and Sealed this

Eleventh Day of November 1980

[SEAL]

Attest:

SIDNEY A. DIAMOND

Attesting Officer     Commissioner of Patents and Trademark